US011648367B2

(12) United States Patent
Maier

(10) Patent No.: US 11,648,367 B2
(45) Date of Patent: May 16, 2023

(54) AIRWAY INHALANT NEBULIZER DEVICE

(71) Applicant: Nathan Christopher Maier, Hayward, CA (US)

(72) Inventor: Nathan Christopher Maier, Hayward, CA (US)

( * ) Notice: Subject to any disclaimer, the term of this patent is extended or adjusted under 35 U.S.C. 154(b) by 825 days.

(21) Appl. No.: 16/700,833

(22) Filed: Dec. 2, 2019

(65) Prior Publication Data

US 2021/0162161 A1 Jun. 3, 2021

(51) Int. Cl.

| | |
|---|---|
| *A61M 16/14* | (2006.01) |
| *A61M 16/20* | (2006.01) |
| *A61M 16/10* | (2006.01) |
| *A61M 16/06* | (2006.01) |
| *A61M 16/04* | (2006.01) |

(52) U.S. Cl.
CPC ...... *A61M 16/147* (2014.02); *A61M 16/0488* (2013.01); *A61M 16/0666* (2013.01); *A61M 16/107* (2014.02); *A61M 16/109* (2014.02); *A61M 16/142* (2014.02); *A61M 16/208* (2013.01); *A61M 2205/123* (2013.01); *A61M 2205/3653* (2013.01); *A61M 2205/52* (2013.01); *A61M 2205/6009* (2013.01); *A61M 2205/6072* (2013.01)

(58) Field of Classification Search
CPC .... A61M 11/06; A61M 15/00; A61M 15/009; A61M 16/10; A61M 16/12–127; A61M 16/14–16; A61M 16/20–209; A61M 11/042; A61M 11/044
See application file for complete search history.

(56) References Cited

U.S. PATENT DOCUMENTS

| | | | | |
|---|---|---|---|---|
| 3,726,274 A * | 4/1973 | Bird | A61M 16/127 | 128/205.24 |
| 3,990,441 A * | 11/1976 | Hoyt | A61M 16/109 | 261/DIG. 65 |
| 5,099,833 A * | 3/1992 | Michaels | A61M 16/0833 | 128/200.14 |
| 5,458,135 A * | 10/1995 | Patton | A61M 11/002 | 128/200.14 |
| 5,603,314 A | 2/1997 | Bono | | |
| 5,813,401 A | 9/1998 | Radcliff et al. | | |
| 9,022,027 B2 | 5/2015 | Addington et al. | | |

(Continued)

*Primary Examiner* — Joseph D. Boecker
*Assistant Examiner* — Thomas W Greig
(74) *Attorney, Agent, or Firm* — Mark Prostik; Thomas Schneck

(57) ABSTRACT

A nebulizer device aerosolizes (or vaporizes) liquid drawn from a liquid reservoir via a fluid flow path into a nebulization chamber. An inlet port is coupled to an external air supply and leads through a check valve and Venturi nozzle (e.g. a duckbill valve) into the chamber to direct an air stream across an opening of the fluid flow path. A discharge port leads from the chamber to a user mask, mouthpiece or canula, where the aerosol or vapor mixture can be inhaled. A filtered outlet port isolates exhaled material from the external environment. Multiple discrete heating elements may be placed around the fluid flow path to preheat the liquid. If the liquid is sufficiently volatile, heating may vaporize the material which can condense back into an aerosol after mixing with the air stream. A set of check valves direct one-way fluid flow and prevent leakage or spillage of material from the device.

27 Claims, 13 Drawing Sheets

(56) References Cited

U.S. PATENT DOCUMENTS

Figure 1:
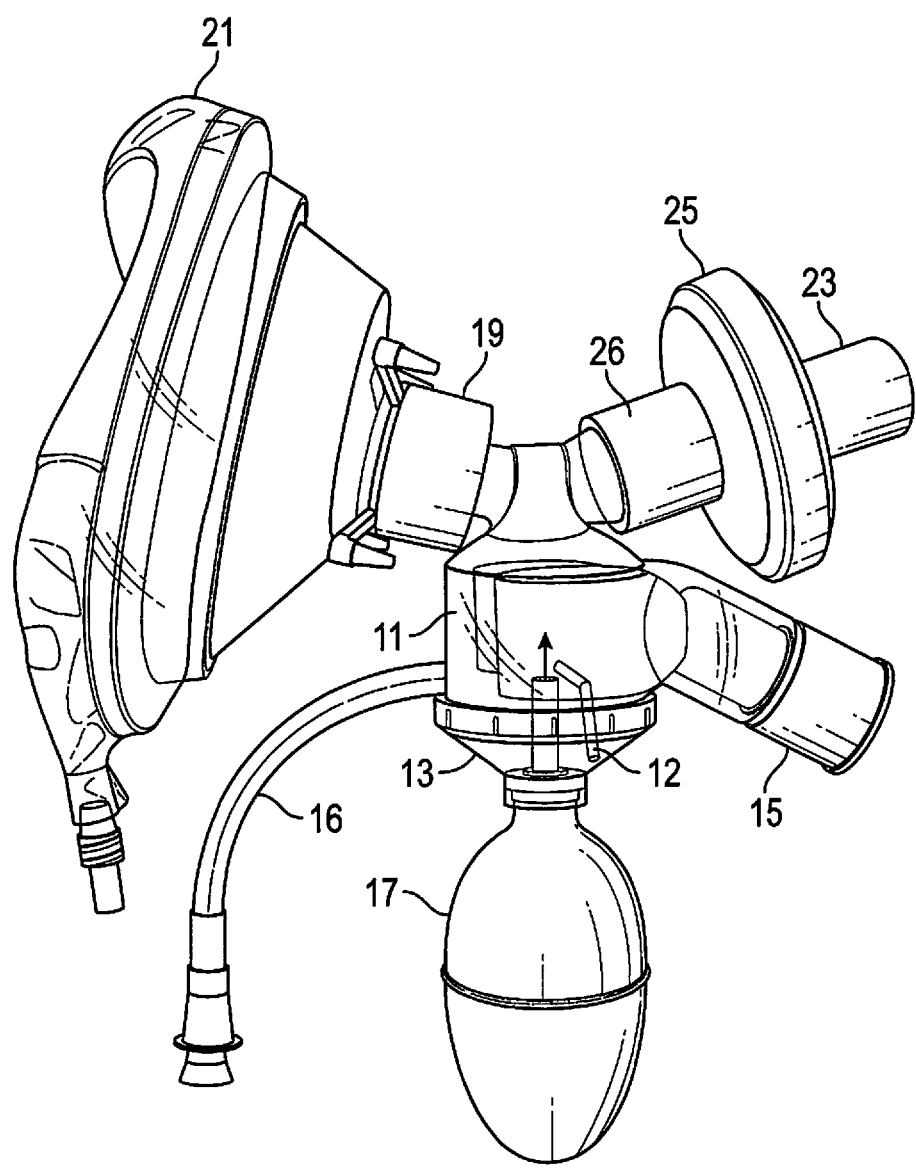
Figure 2:
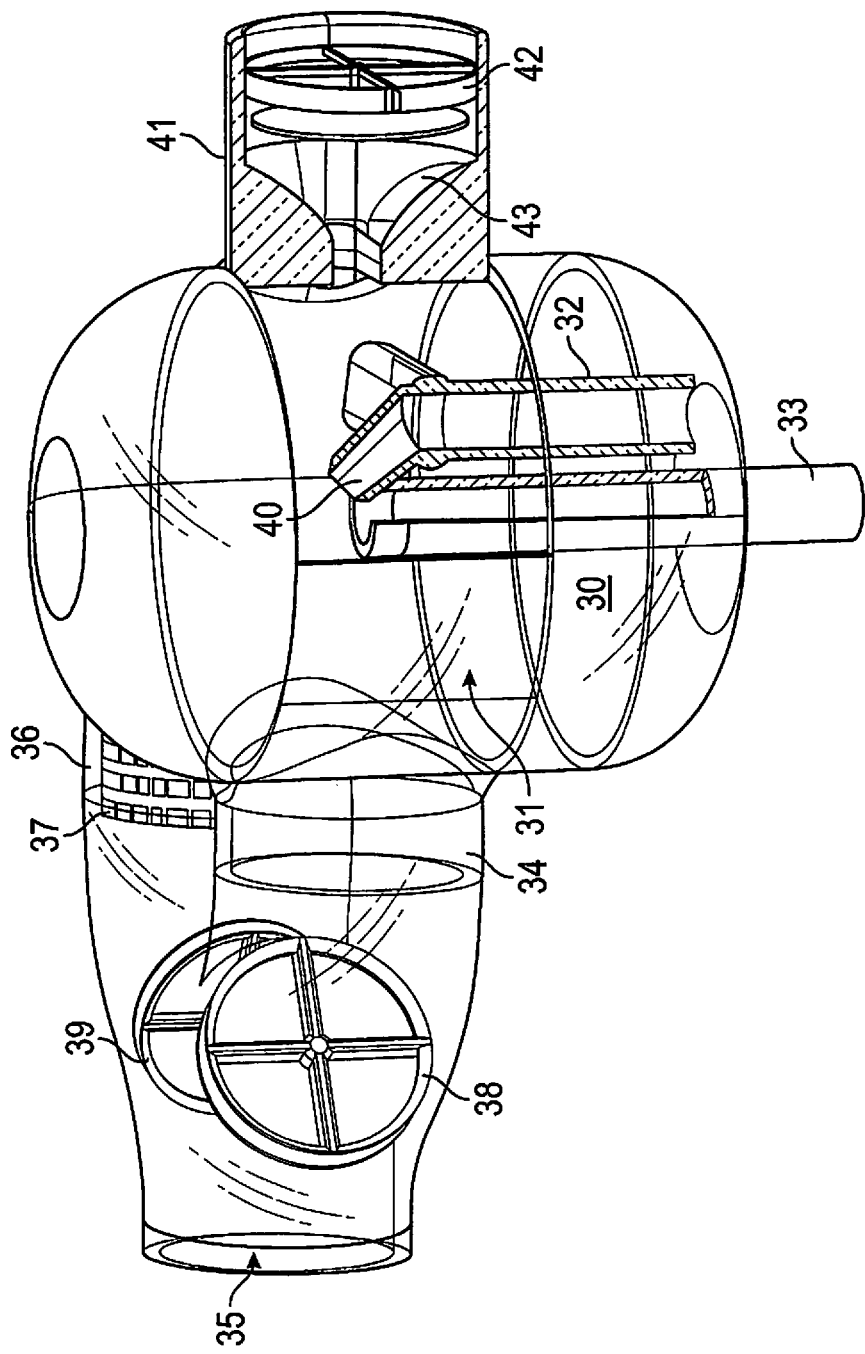
Figure 3:
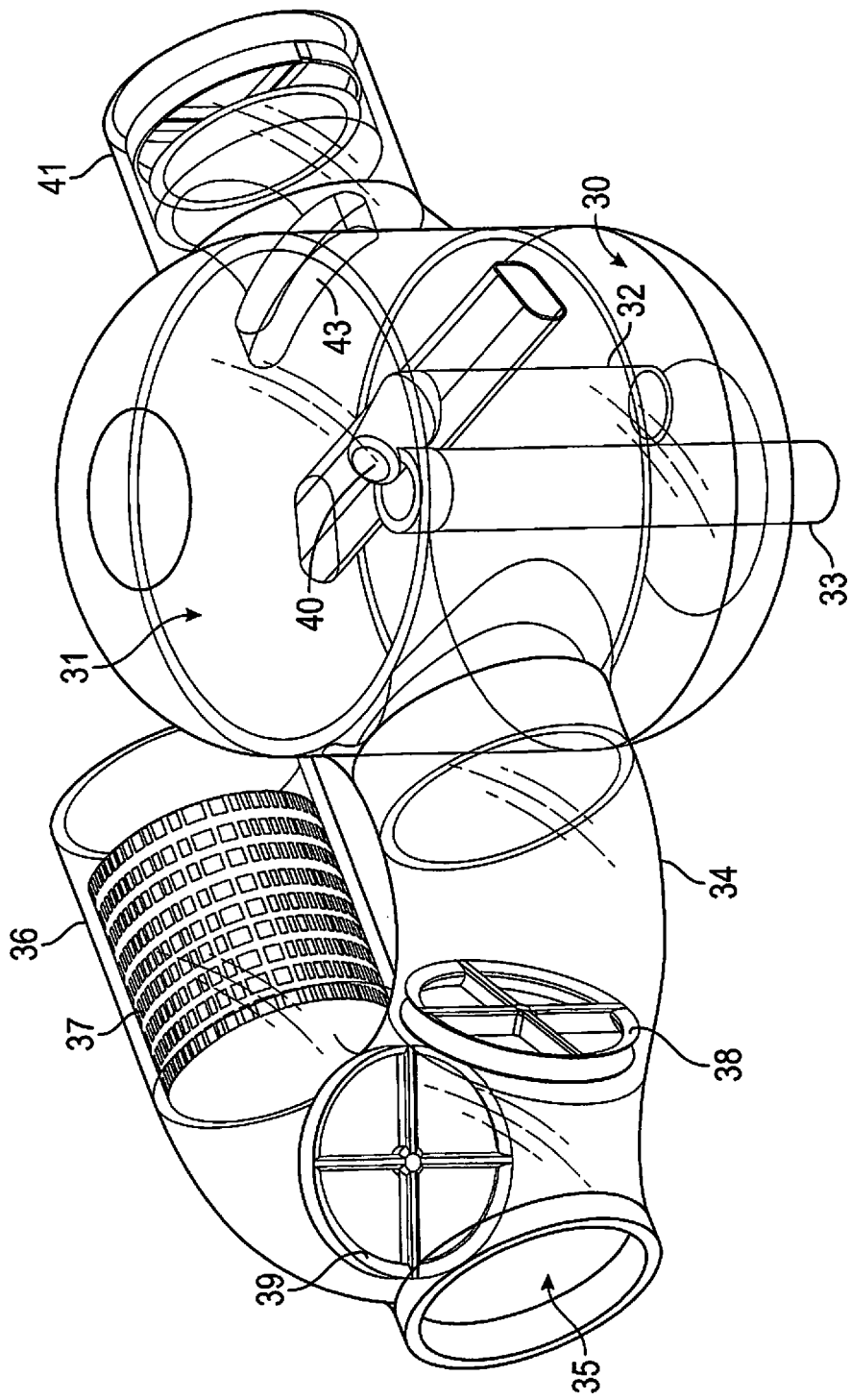
Figure 4:
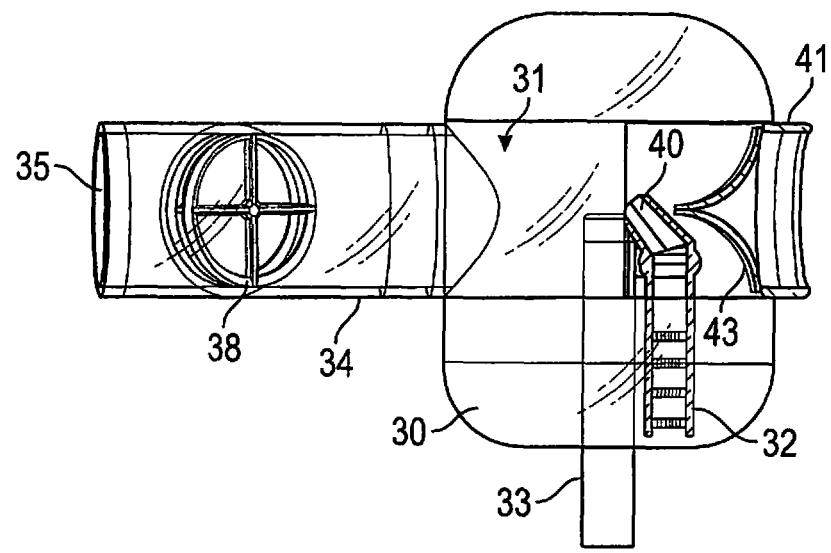
Figure 5:
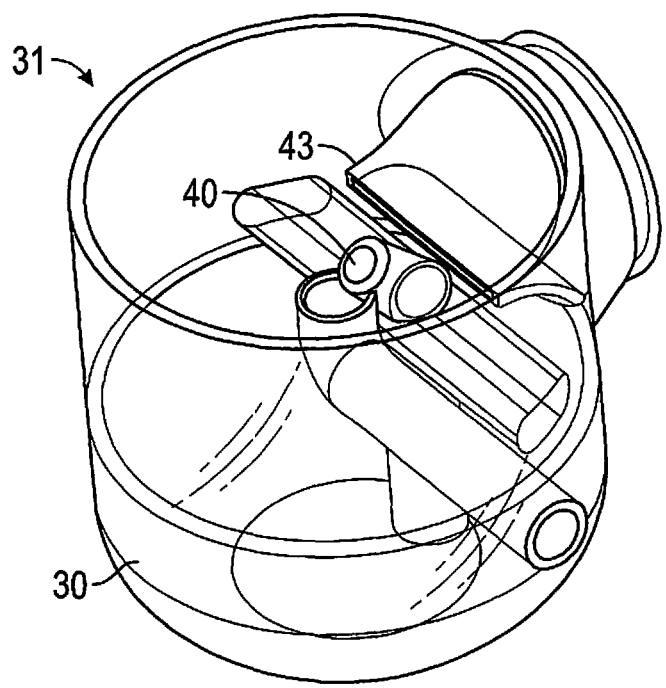

| | | |
|---|---|---|
| 9,566,397 B2 | 2/2017 | Faram |
| 2002/0157663 A1* | 10/2002 | Blacker .................. A61M 11/00 128/200.21 |
| 2005/0263150 A1 | 12/2005 | Chathampally et al. |
| 2019/0192790 A1 | 6/2019 | Toddywala et al. |

* cited by examiner

AIRWAY INHALANT NEBULIZER DEVICE

TECHNICAL FIELD

The present invention relates to apparatus for delivering nebulized aerosol or vapor to a patient for inhalation, e.g. for the administration of medication.

BACKGROUND ART

In U.S. Pat. No. 5,603,314, Bono describes an aerosol inhalation device for delivering aerosol mist to a patient. The device comprises a nebulizer that generates and delivers an aerosol through a first conduit to the patient, and a filter that captures exhaled droplets received through a second conduit from the patient before passing now contaminant-free gas to an exhaust port.

In U.S. Patent Application Publication No. 2005/0263150, Chathampally et al. describes a system for administration of medications to a patient via a nebulizer in combination with an airtight face mask. The nebulizer, which is either an ultrasonic nebulizer or a jet nebulizer, produces a mist of medication-containing droplets. The nebulizer is connected to the face mask at a first one-way valve. A filtration unit, connected to the face mask at a second one-way valve, scavenges medications that would otherwise escape into the patient's immediate surroundings.

SUMMARY DISCLOSURE

A nebulizer or vaporizer device is equipped with several one-way check valves at key locations to prevent loss or spillage of fluid contained within a liquid reservoir of the nebulizer until required to be inhaled as aerosol or vapor by a user. The nebulizer chamber is equipped with an inlet port leading through a check valve and Venturi nozzle arranged to direct an air stream across an opening in the fluid flow path. In one embodiment, the check valve and Venturi nozzle together comprise a duckbill valve, which may be provided with ribs parallel to airflow within a throat of the valve/nozzle and with a thicker ring of rigid material around exit lips of the duckbill valve. When the liquid reservoir is a substantially sealed cartridge, an air intake into the liquid reservoir admits air from the nebulizer chamber to replace the fluid drawn through the fluid flow path to avoid vacuum lock between the reservoir and chamber. Both the reservoir's air intake and the fluid flow path have one-way check valves to prevent leakage of liquid if the device were to be inverted.

Additionally, a fluid flow path between the reservoir and the device's nebulization chamber may be heated by multiple discrete heating elements t at can be provided around that flow path. The fluid flow path may contain thermally conductive mesh at least at locations inwardly adjacent to the discrete heating elements to better transfer heat toward the center of the flow path, and wicking material may be packed between the mesh. This heating can be provided to raise the temperature of the fluid to a comfortable body temperature (e g. 37° C.) or to a temperature selected to reduce vapor pressure and thereby enhance nebulization efficiency, or even to fully vaporize the fluid if the material is sufficiently volatile that it would not be too hot for safe inhalation. To protect the contents of the liquid reservoir, thermal insulation may be provided both between and radially outward around the heating elements.

There are basically three main types of embodiment, a pure nebulizer, a hybrid nebulizer, and a pure vaporizer. In the pure nebulizer, a source of highly pressurized air (from a pump or compressed air source) passes over a small Venturi nozzle at the opening or tip of the fluid flow path to nebulize liquid material drawn up through the flow path from a reservoir or cartridge. In a hybrid nebulizer, heating elements are provided around the fluid flow path to apply enough heat to lower the vapor pressure in the flow path so that effective nebulization is possible with liquids that would not otherwise be possible to nebulize, or to reduce the needed velocity of the air stream passing over the opening to cause the nebulization. In a pure vaporizer, enough heat could be added to vaporize the liquid material in the flow path so that nebulization by a high velocity air stream is not even necessary. In that case, the air stream simply serves to mix with the vapor and direct the mixture out of the chamber to the user.

BRIEF DESCRIPTION OF THE DRAWINGS

FIG. 1 is side perspective view of a manually operated nebulizer device in accord with the present invention.

FIGS. 2 and 3 are two different perspective views from above of a second embodiment of a nebulizer in accord with the present invention.

FIG. 4 is a side elevational view of the second embodiment of FIGS. 2 and 3.

FIG. 5 is a partial open perspective view of the nebulization chamber in the embodiment of FIGS. 2 through 4.

FIG. 6 is a perspective view from above of a third embodiment of a nebulizer (or vaporizer) in accord with present invention that includes heating elements.

FIG. 7 is a perspective view of a liquid reservoir cartridge for use with any of the embodiments of the present invention.

FIGS. 8 and 9 are respective top plan and side perspective views of the third embodiment of the present invention.

FIG. 10A is a perspective view of liquid reservoir cartridge with a readable barcode or punch code. That code could provide information to a heater control circuit, such as optimal heating parameters (temperature, etc.) for the multiple discrete heating elements of the third embodiment, as well as manufacturer lot number, and authorization codes to prevent use of unapproved cartridges or reuse of refilled cartridges.

FIG. 10B is a perspective view of a liquid reservoir cartridge with a readable and writable RFID tag to provide the heater control circuit with the same kinds of information as the cartridge in FIG. 10A.

FIGS. 11 and 12 are side sectional views of heated fluid flow paths for the third embodiment of the present invention, the first version in FIG. 11 using solid heating rings and the second version in FIG. 12 using heating coils.

FIGS. 13 and 14 are two different perspective cutaway views of the heated fluid flow paths for the third embodiment, which include a ball valve therein.

FIGS. 15 and 16A are respective side sectional views of two versions of a check valve and Venturi nozzle combination on an inlet port to any of the embodiments of the present invention. FIG. 16B is sectional view of the nozzle taken along the line 16B-16B in FIG. 16A.

DETAILED DESCRIPTION

With reference to FIG. 1, a first embodiment of a nebulizer device in accord with the present invention comprises a nebulization chamber 11 with a liquid reservoir 13 connected via a fluid flow path 12 to the nebulization chamber 11, an inlet port and check valve 15 leading into the nebulization chamber 11 to provide a flow of accelerated air, in this case by means of a manually operated squeeze bulb 17, a discharge port 19 for aerosolized liquid leading through an air pathway into a user mask 21, and a filtered outlet port 23 from the user mask 21 for exhaled air, where the filter is contained within the enlarged volume 25. A check valve 26 in the outlet flow path prevents air being drawn in from the discharge side during inhalation. Internal features of the nebulization chamber 11 and of the various connecting pathways and ports are essentially as described below in more detail for the other embodiments, in that various one-way check valves are provided for the ports or pathways to minimize or eliminate any leakage of active liquid material and to ensure that the inhaled and exhaled air flow through the proper pathways, and in that accelerated air is directed across the opening of the fluid flow path 12 leading from the liquid reservoir to cause nebulization into an aerosol that can be inhaled by an patient through the mask 21. The mask 21 is sealed to ensure that inhaled material does not escape into the external environment. A mouthpiece or nasal canula could also be used instead of the mask 21.

Instead of a squeeze bulb 17 to move air through the nebulization chamber 11, a hand or foot operated bellows could be provided, or a small gas canister, or (as in other embodiments described below) a pressurized air supply line. All these sources of accelerated air flow are functionally equivalent, and except perhaps for different sizes and proportions of internal features of the nebulization chamber 11 to ensure adequate flow velocity and efficient nebulization are substantially identical.

With reference to FIGS. 2-5, another embodiment of a nebulizer in accord with the invention illustrates in more detail a version of the internal components of a nebulization chamber 31. As in FIG. 1, there is a discharge port 34 leading from the chamber 31 through an air pathway 35 to a user mask, mouthpiece, or nasal cannula (not shown). A check valve 38 is provided for one-way flow of aerosol material from the discharge port 34 toward that mask. Likewise, there is an outlet port 36 containing a filter 37 (such as a HEPA filter or an activated charcoal filter), again with a check valve 39 providing one-way flow of exhaled air from the user mask to the outlet port 36.

In this embodiment, the bottom of the nebulization chamber 31 forms a liquid reservoir 30. A fluid flow path 32 extends from near the bottom of the reservoir 30 upwards to an opening 40. An inlet port 41 coupled to an external air supply leads through a check valve 42 and a Venturi nozzle 43 that directs a stream of accelerated air across the opening 40 of the fluid flow path 32. The nebulization device works with a non-pressurized air supply at atmospheric pressure, but a pressurized air supply could also be used, e.g. to assist those patients that have a compromised respiratory system. The check valve 42 serves mainly to prevent liquid in the chamber from leaking out in the event the nebulizer is tipped over.

Pressurized air source 33 provides high velocity air over the fluid path opening 40 to form very small droplets or mist. A stream of air enters through the inlet port 41 and is accelerated to high velocity by the Venturi nozzle 43. The high velocity air stream from the nozzle 43 carries the aerosolized material out of the chamber 31 through the discharge port 34 and to the user mask.

Figure 6:
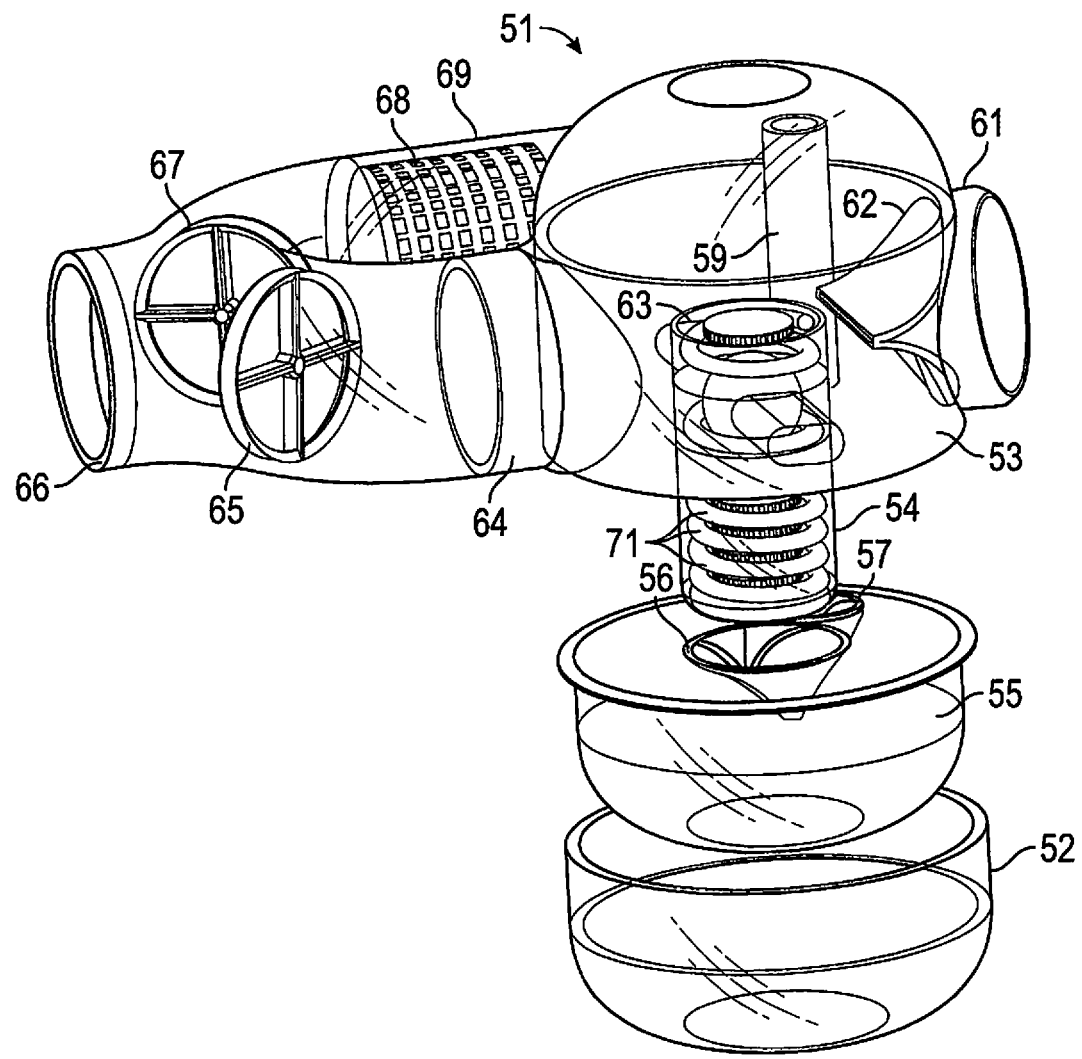

With reference to FIG. 6, another embodiment of a nebulizer in accord with the present invention, which may be either a hybrid (heat-assisted) nebulizer or a pure vaporizer device 51 (depending upon the liquid material and the amount of heating), features a heating system 71 around the fluid flow path 54 that applies heat to material drawn from the liquid reservoir 55 and flowing within the flow path 54. In the case of a hybrid nebulizer, the heating system 71 applies heat to the liquid in the flow path 54 to lower the vapor pressure so that nebulization can be effectively achieved with liquid materials that would not otherwise be possible with pure nebulizers as in FIGS. 1-5. In the case of a pure vaporizer, as opposed to a pure nebulizer or a hybrid (heat-assisted) nebulizer, enough heating could be applied to the liquid drawn from the reservoir sufficient to create a vapor in the fluid flow path. In that case, nebulization of the now already vaporized material is not necessary, so that neither a highly pressurized air supply path (from a pump or compressed source) nor a high-velocity air stream is required. In that case, the air stream from the nozzle 62 is merely provided to mix with the vaporized material and help direct that mixture out of the chamber 53 to a user.

Figure 7:
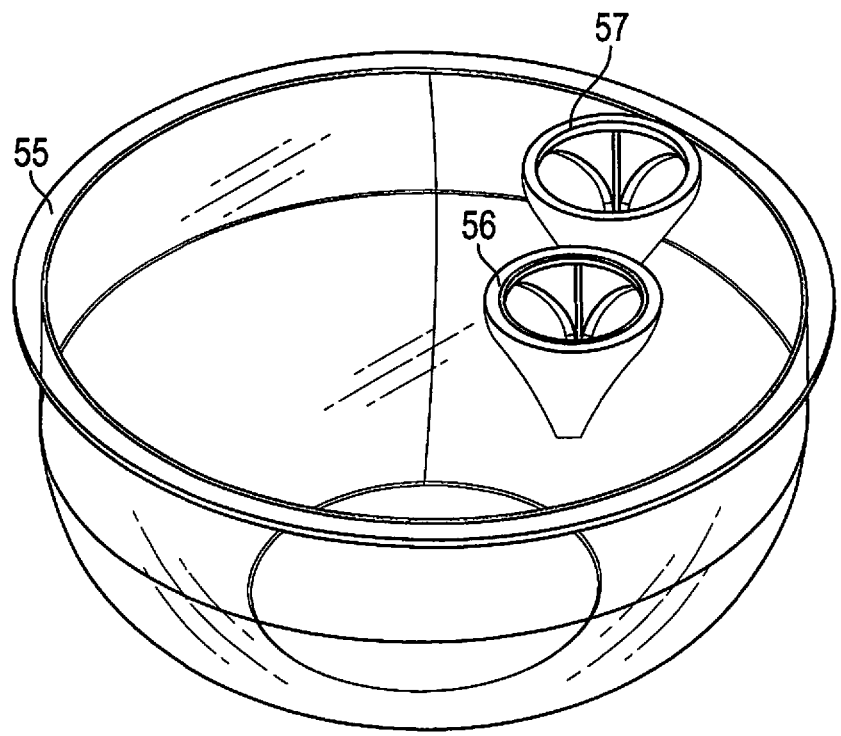

Also, the liquid reservoir can be provided in the form of an attachable reservoir cartridge 55, instead of simply storing the liquid at the bottom of the chamber 53. Not only does this prevent sloshing of liquid about the chamber 53 but, in the case of heated devices like that shown in FIG. 6, more effectively isolates the liquid material from unnecessary heating until it is drawn up through the flow path 54. The bottom 52 of the chamber 53 can be detached to allow insertion of a new cartridge 55 therein. As seen also in FIG. 7, the cartridge 55 may have a set of check valves 56 and 57 that can prevent leakage of liquid from the reservoir 55 in the event the cartridge were to be tilted or inverted, while still allowing adequate flow of liquid material into a fluid flow path 54 and admission of replacement air into the cartridge 55 to prevent vacuum lock.

Figure 8:
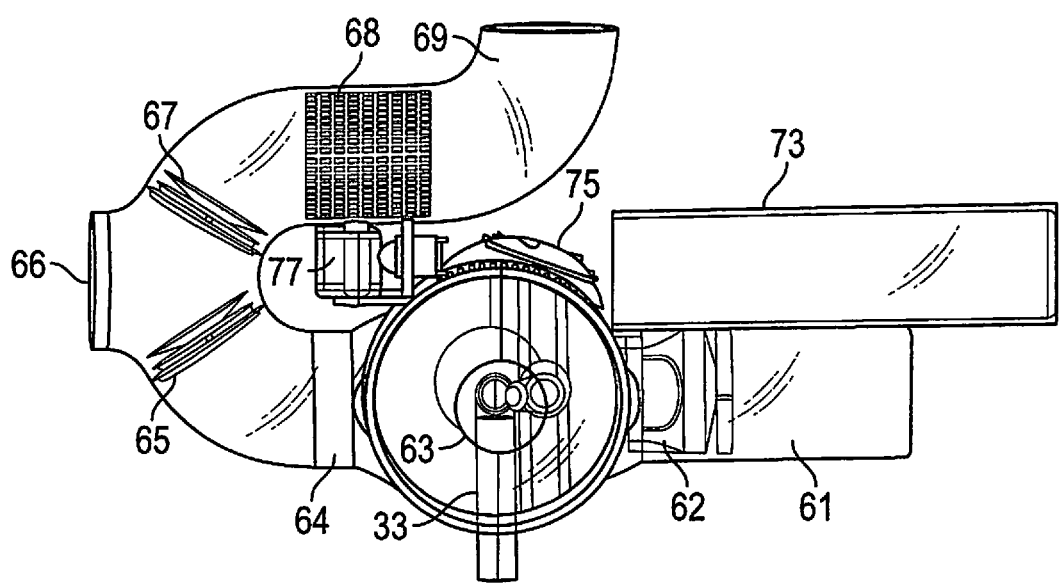
Figure 9:
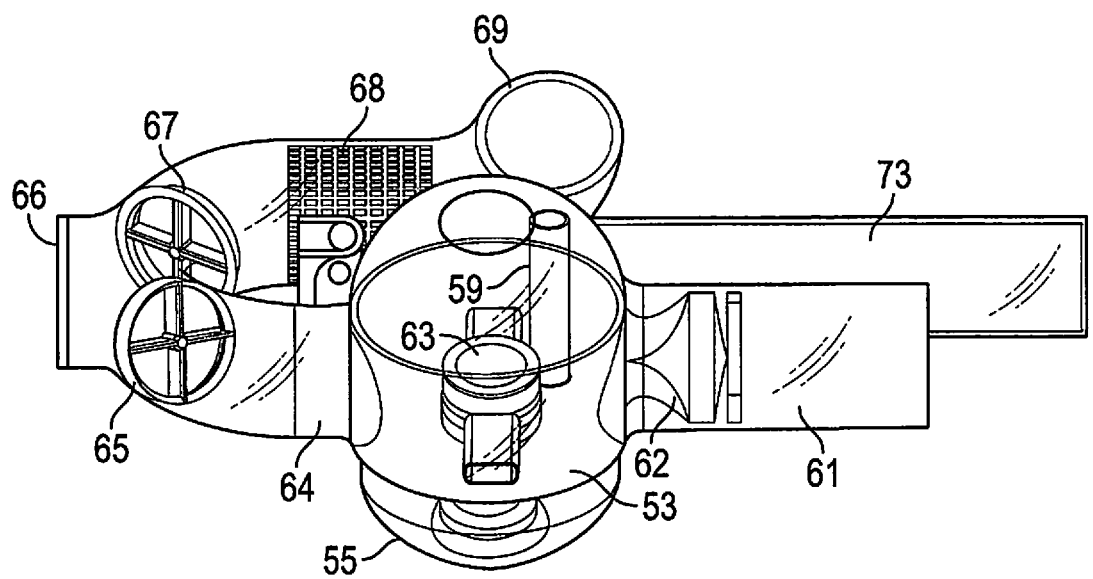

As in the previous embodiments, and as also seen in FIGS. 8 and 9, an inlet port 61 with check valve and Venturi nozzle 62 produces a high velocity airstream for carrying nebulized material drawn from the reservoir cartridge 55 out of fluid flow path opening 40 and nebulized by pressurized air source 33 in FIG. 8, or alternatively for carrying vaporized material drawn from the reservoir cartridge 55 out of the top vaporizer opening 63 of the heated fluid pathway 54 in FIG. 9.

The one-way check valve and Venturi nozzle 62 may together comprise a duckbill valve, which is an option for any of the embodiments and will be discussed further below. An air intake 59 admits air from the top, sides or bottom of the chamber 53 and into the cartridge 55 through the check valve 57. A discharge port 64 exits the chamber 53 and leads through a check valve 65 and an air pathway 66 to a user mask (not shown). Exhaled air is directed from the user mask through the air pathway 66 and check valve 67 to a filter 68 and outlet port 69.

As seen in FIG. 6 (but also in more detail in FIGS. 11 to 14, discussed further below), multiple discrete heating elements 71 are spaced around the fluid flow path 54. In this way, the liquid drawn up through the flow path 54 may be heated prior to nebulization at the top opening 63. The liquid could be heated, e.g., close to normal human body temperature (37° C.) to ease the body's response to the aerosol being inhaled into the lungs. This reduces the chances of lung spasms in response to inhaling a cold aerosol mist, facilitates better bio-uptake of the intended medicinal material in the lungs (e.g. the body responds better to certain anesthetics if they are at body temperature), and more generally increases user comfort. Note that the Venturi effect itself causes the airstream to chill as it is accelerated by the nozzle 62 and then directed across the opening 63, so preheating of the liquid drawn through the flow path 54 is beneficial to restoring a more useful and comfortable temperature. Still further, heating of the liquid reduces the vapor pressure and thereby enhances nebulization efficiency. Finally, assuming the liquid material is adequately volatile, so that overly hot temperatures are not required, the heating can actually vaporize the material as it is drawn up through the flow path 54 for mixing with the airstream from the nozzle 62. It could then subsequently re-condense into an aerosol mixture as it interacts with the airstream and cools.

Since the heating elements require electricity and corresponding electrical and thermal control, inlet ports for the electrical pathways will be provided. A lithium ion battery pack 73 could supply the electrical power for the controlled heating, as seen in FIGS. 8 and 9, where for example the battery pack 73 is conveniently attached to the inlet port 61. A control circuit board 75 and a thumb activated trigger switch 77 (in some embodiments including a fingerprint sensor to prevent unauthorized use) could likewise be attached at any convenient location on the exterior of the device. In some embodiments the control circuit board 77 could require activation of the user's authorized fingerprint at a point-of-sale location or other location approved to verify the user's government issued ID. This would serve to prevent device usage by underaged or non-prescription users.

Figure 10A:
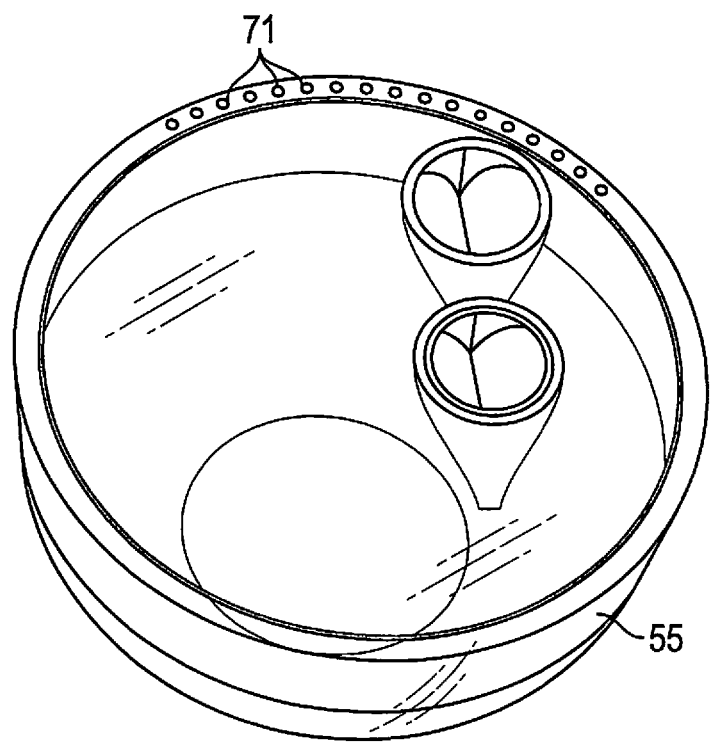

In one possible embodiment, a readable barcode or punch code 71 can be provided on the cartridge, for example on its edge as seen in FIG. 10A, to provide a variety of information specific to the cartridge contents to the heater control 75. This can include heating parameters for the liquid material (such as specific heating zones or profiles of the discrete heating elements around the flow path, maximum temperatures, etc.).

Figure 10B:
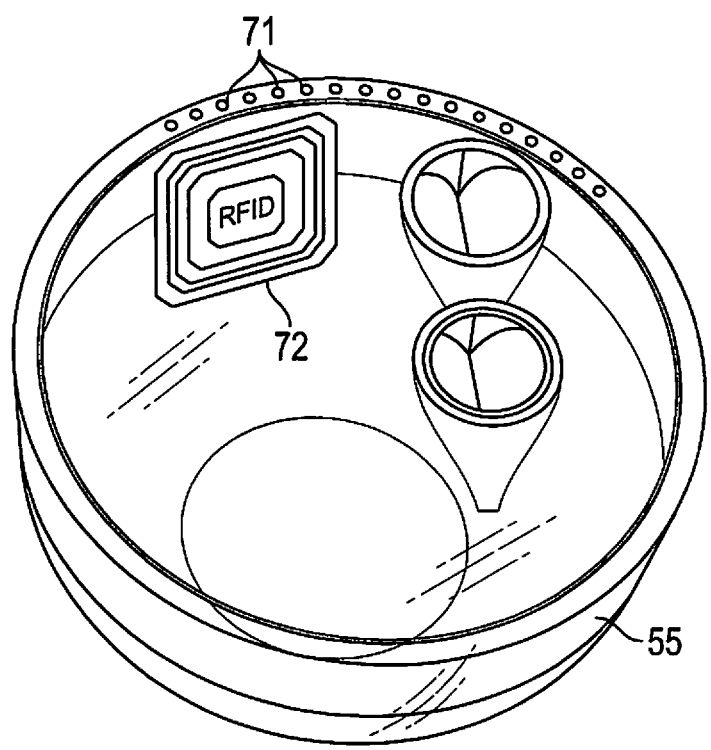
Figure 11:
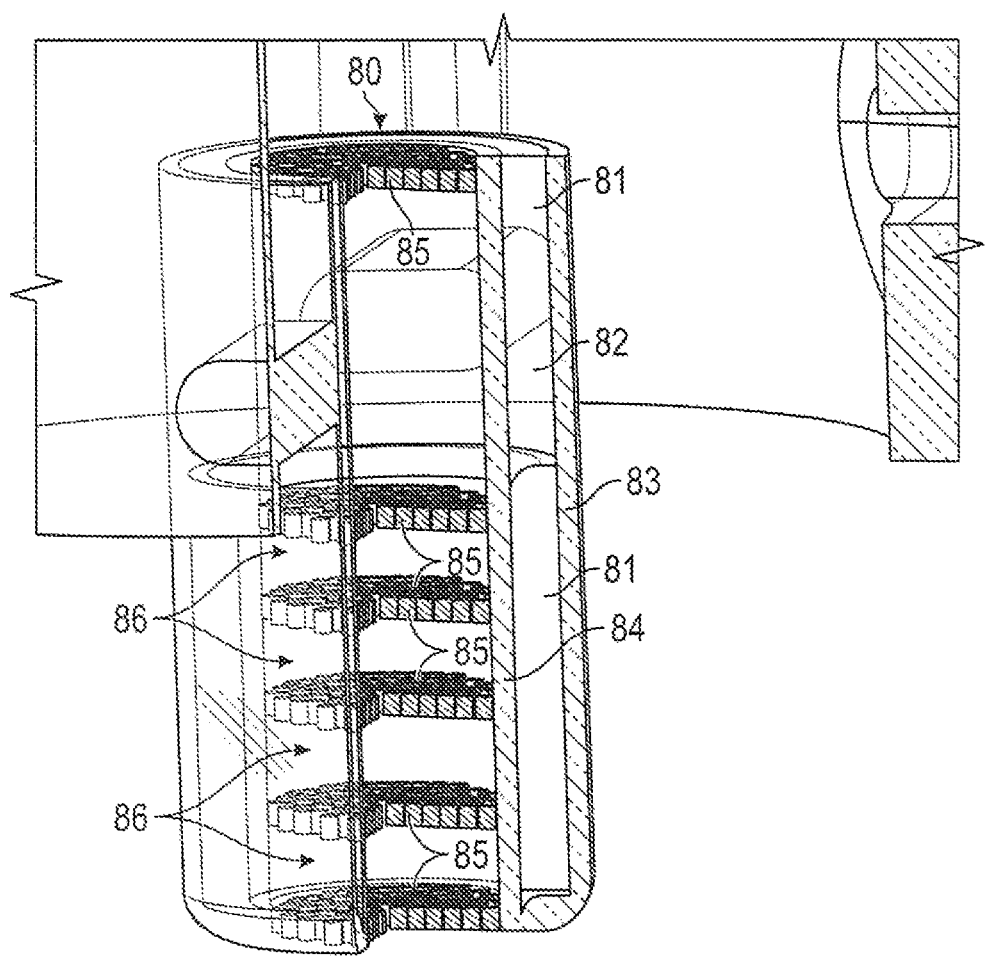

In yet another embodiment, as seen in FIG. 10B, an RFID tag 72 could be included in the cartridge. The nebulizer's or vaporizer's heater control circuit could write to the RFID tag 72 via micro-USB, Bluetooth/WIFI connectivity, or other communication means to record cartridge information updates. Hence, the RFID tag 72 would not only allow storage of much the same kinds of coded information content as the barcode (e.g. specific parameters for heating the cartridge's liquid contents along the flow path) but could also log new information (such as the number of times the cartridge is used or whenever it becomes empty) to prevent unauthorized refilling of a cartridge. Stored information can include manufacturer authorization and batch codes, whereby a heater control circuit could activate a "limp mode" to prevent heating of unknown or adulterated contents. If the RFID coded information does not match manufacturer specifications (e.g. with a cartridge forgery), or the number of recorded uses exceeds some specified reasonable limit, or the cartridge has previously been empty but not refilled by the manufacturer itself, but by some unknown third party, then for user safety the nebulizer or vaporizer, responsive to the RFID coded information could refuse to operate.

Figure 12:
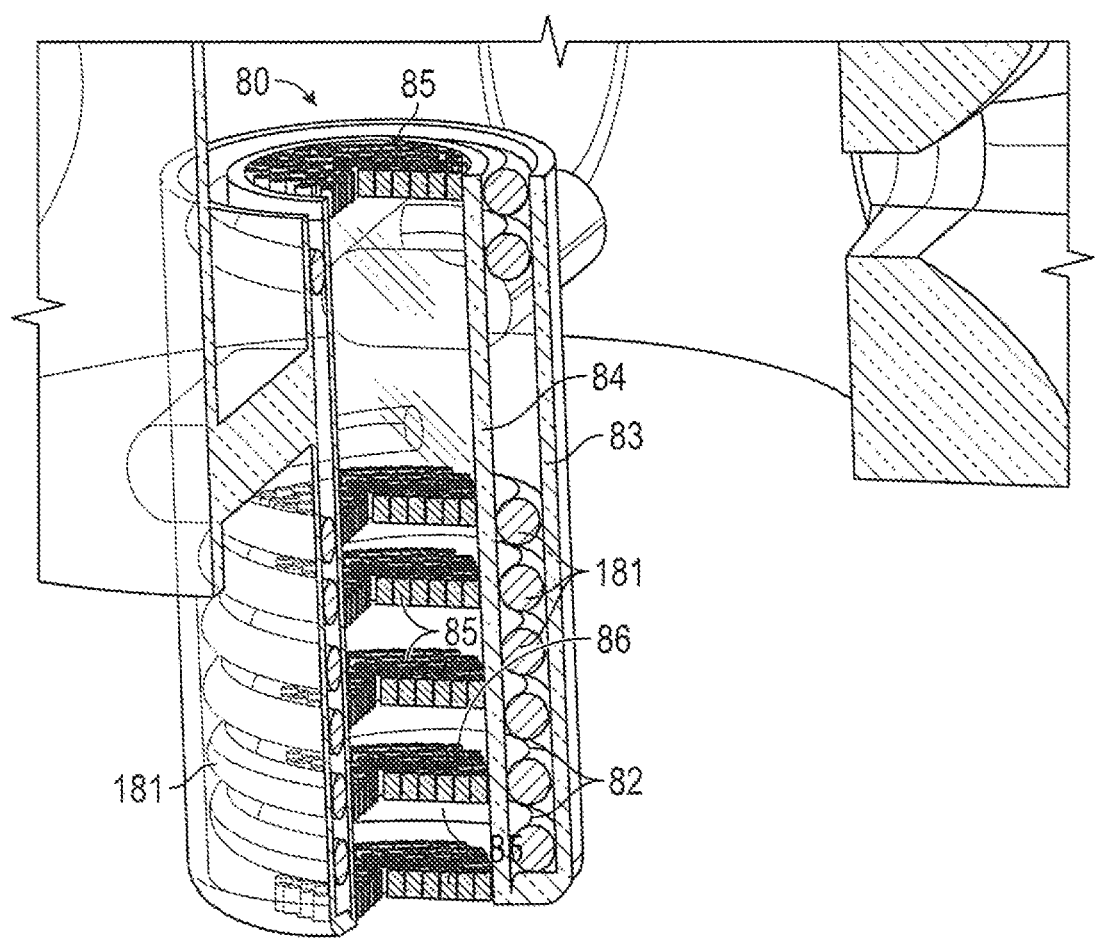
Figure 13:
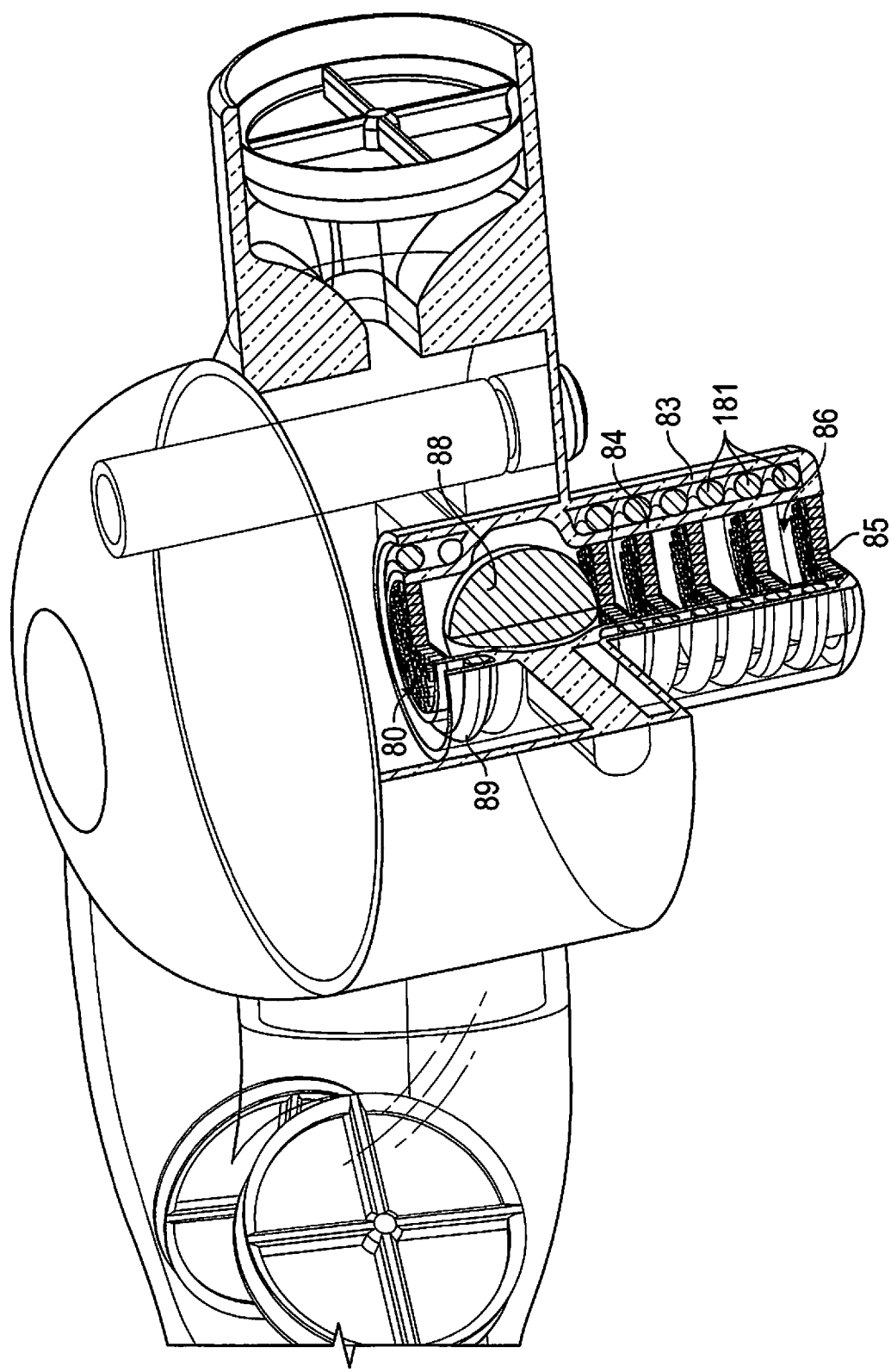
Figure 14:
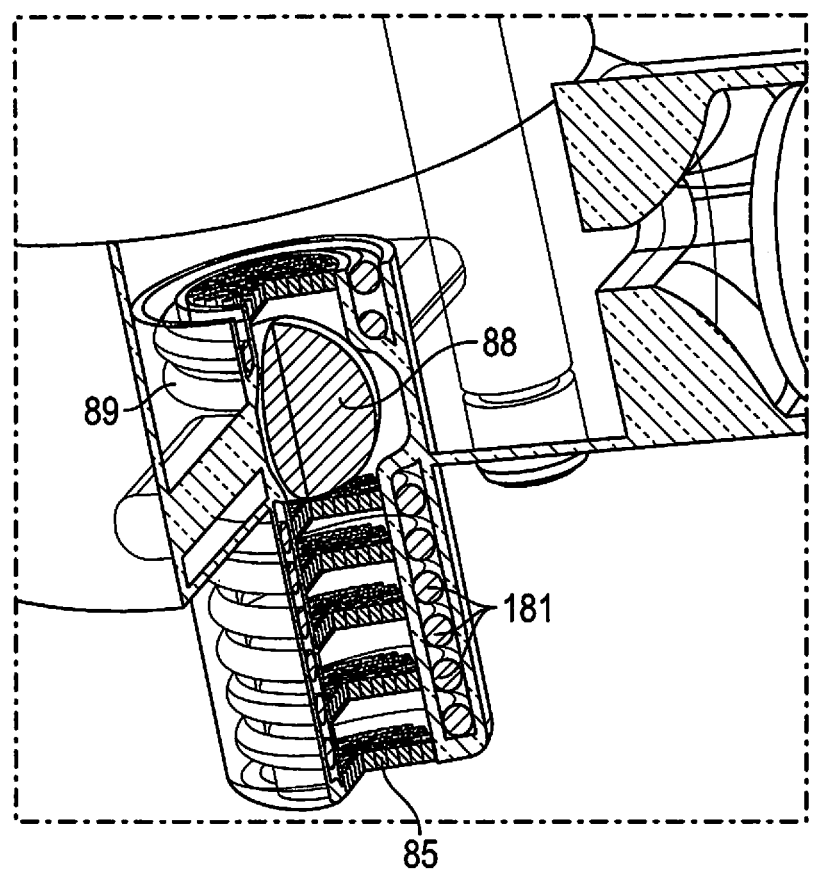

With reference to FIGS. 11-14, multiple discrete heating elements 81 (in this instance, two) surround the core of the fluid pathway 80 to provide gradated levels of heating. The heating elements 81 may be foil or solid rings or could be heating coils 181 as seen in FIGS. 12-14. Spacing 82 between the heating elements 81 reduces heat-soak between elements. An insulating outer liner 83 of ceramic, polyimide or other thermal insulation material may be provided to prevent heat transference into the fluid reservoir itself or into the duckbill valve or other Venturi nozzle where excess heating could cause damage. Only the fluid flow path 80 and the liquid within it should be heated by the elements 81. A liner 84 may be disposed between the heating elements 81 and the flow path 80. This inner liner 84 can serve as a thermal conductor (e.g. stainless steel) or as an insulator (e.g. ceramic or polyimide) depending on specific design intent (e.g., some portions of the liner along the length of the pathway 80 may be conductive and other portions may be insulative to precisely control where the heat is to be transferred into the liquid material, while keeping the liquid in the reservoir cool). Heating mesh 85 is in the fluid path 80 to conduct heat from the liner wall 84 into the center of the flow path 80. This added thermal conductivity removes any need to overheat the liquid along the wall 84 of the passage 80 to compensate for cooler liquid passage along the center of the passage 80. The mesh 85 could instead be in the form of a lattice, coils or filamentary material. It is anticipated that wicking material 86, commonly used in standard vaporizers, could be packed between the heat-conducting mesh/lattice/coils/filaments to assist moving the fluid up through the pathway 80. Since the inner liner 84, the mesh 85, and wicking material 86 are in contact with the liquid material to be nebulized and inhaled by a patient, they will need to be composed of bio-compatible materials to avoid any cross-contamination.

As seen in FIGS. 13 and 14, a ball valve 88 may be part of the fluid supply pathway 80. A weighted ball normally resting one of the conducting mesh elements 85 to allow fluid to pass around the ball, will engage a sealing surface 89 if the device is inverted to prevent leakage of liquid out of the reservoir and flow path. A similar ball valve may also be included in the air return tube. An added advantage to having the ball valve in a heated nebulizer (or vaporization) device is that the ball 88 will be pushed upwards against sealing surface 89 if vapor flow is very strong and therefore act as a check against too hot material from being inhaled and burning the mouth, throat or lungs of a patient.

Figure 15:
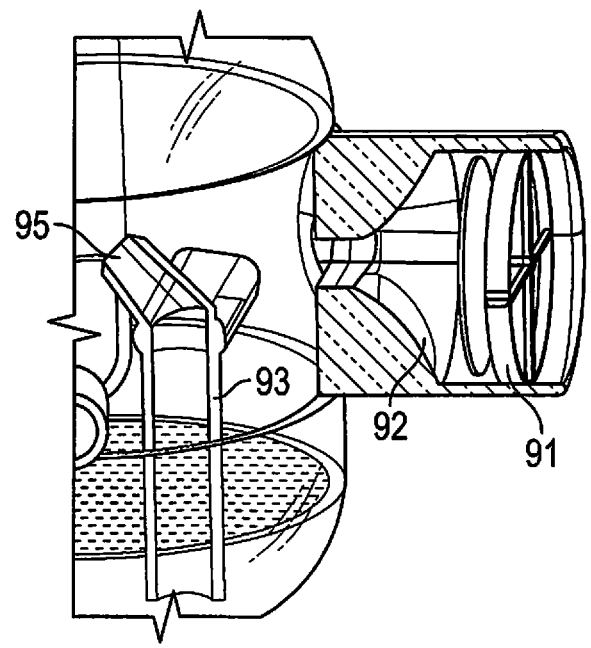
Figure 16A:
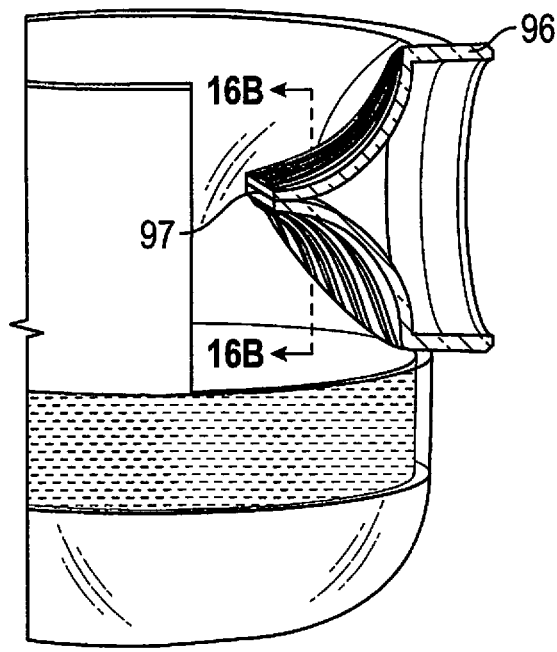
Figure 16B:
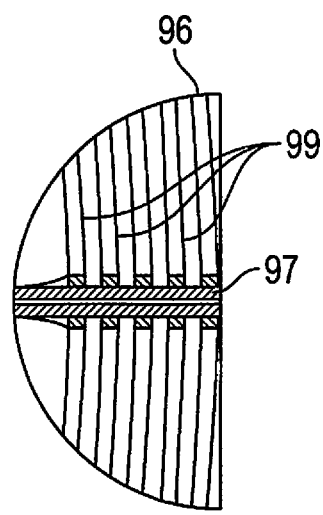

With reference to FIGS. 15 and 16A, two versions of the check valve and Venturi nozzle are shown. In FIG. 15, a check valve 91 and Venturi nozzle 92 are separate components and the Venturi nozzle 92, while serving as a partial check valve, is mainly provided for its acceleration of the incoming airstream into a directed high velocity stream across the top opening 95 of the fluid flow path 93. Since some liquid could leak through the nozzle 92 if the device is tilted, the check valve 91 is provided to block any liquid from splashing out of the nebulizer device. Alternatively, in FIG. 16A, the check valve and Venturi nozzle are combined into a single duckbill check valve 96 whose beak 97 has a sufficiently narrow opening that liquid cannot substantially leak out. The duckbill valve 96 is shaped to serve the dual function as a nozzle that accelerates airflow over the supply pathway's opening. It has a nozzle shape to create a Venturi effect on air flowing through it. To enhance its performance, a set of ribs 99 parallel to the airflow may be provided on the interior throat or bill of the valve 96 to ensure laminar flow toward the beak opening, as seen in the FIG. 16B cross-section. Additionally, the beak opening 97 of the valve 96 may, in some cases, be thickened to form a ring of material around the opening 97 that will maintain the widened shape of the opening to create the ribbon of accelerated laminar-flow air (rather than stretching into an annular shape) as well as make it more rigid and avoid any vibratory opening and shutting of the opening.

What is claimed is:
1. A nebulizer comprising:
   a nebulization chamber;

a liquid reservoir connected via a fluid flow path to the nebulization chamber;

an external air supply arranged to direct high pressure air across an opening of the fluid flow path in the nebulization chamber;

an inlet port coupled to an external air supply and leading through a check valve which includes a Venturi nozzle portion into the nebulization chamber arranged to direct accelerated air across the opening of the fluid flow path in the nebulization chamber, wherein the check valve with Venturi nozzle portion together comprise a duckbill valve;

a discharge port leading from the nebulization chamber through an air pathway to a user mask; and a filtered outlet port from the user mask.

2. A nebulizer as in claim 1, wherein the duckbill valve has ribs on a throat of the duckbill valve which are parallel to airflow through the valve.

3. A nebulizer as in claim 1, wherein the duckbill valve has a thicker ring of rigid material around exit lips of the duckbill valve.

4. A nebulizer as in claim 1, wherein another check valve is provided within the fluid flow path.

5. A nebulizer comprising:
a nebulization chamber;
a liquid reservoir connected via a fluid flow path to the nebulization chamber, wherein the liquid reservoir has an air return vent with a check valve to admit air into the reservoir while preventing leakage of fluid from the reservoir;

an external air supply arranged to direct high pressure air across an opening of the fluid flow path in the nebulization chamber;

an inlet port coupled to an external air supply and leading through a check valve which includes a Venturi nozzle portion into the nebulization chamber arranged to direct accelerated air across the opening of the fluid flow path in the nebulization chamber;

a discharge port leading from the nebulization chamber through an air pathway to a user mask; and a filtered outlet port from the user mask.

6. A nebulizer as in claim 5, further comprising multiple discrete heating elements around the fluid flow path.

7. A nebulizer as claim 6, wherein thermal insulation is provided between the discrete heating elements parallel to line of flow in the fluid flow path.

8. A nebulizer as in claim 6, wherein thermal insulation is provided radially outward around the heating elements to minimize heating of the liquid reservoir.

9. A nebulizer as in claim 6, wherein the fluid flow path has thermally conductive mesh therein at least at locations inwardly adjacent to the discrete heating elements.

10. A nebulizer as in claim 9, wherein wicking material is packed between the thermally conductive mesh.

11. A nebulizer as in claim 6, wherein fluid from the liquid reservoir is heated in the fluid flow path to 37° C.

12. A nebulizer as in claim 6, wherein fluid from the liquid reservoir is heated in the fluid flow path to a temperature selected to reduce vapor pressure and thereby enhance nebulization efficiency.

13. A nebulizer as in claim 6, wherein fluid from the liquid reservoir is heated in the fluid flow path to vaporization.

14. A nebulizer comprising:
a nebulization chamber;
a liquid reservoir connected via a fluid flow path to the nebulization chamber, wherein the liquid reservoir is a cartridge removable from the nebulization chamber, the cartridge with a first valve coupled to the fluid flow path, the cartridge further having an air return vent with second valve to admit air into the cartridge as liquid is drawn from the cartridge into the fluid flow path;

an external air supply arranged to direct high pressure air across an opening of the fluid flow path in the nebulization chamber;

an inlet port coupled to an external air supply and leading through a check valve which includes a Venturi nozzle portion into the nebulization chamber arranged to direct accelerated air across the opening of the fluid flow path in the nebulization chamber;

a discharge port leading from the nebulization chamber through an air pathway to a user mask; and a filtered outlet port from the user mask.

15. A nebulizer as in claim 14, wherein the cartridge has a readable coded information element thereon, coded information stored on the readable element including at least information reading heating parameters specific to liquid contained in the cartridge.

16. A nebulizer as in claim 15, wherein additional coded information stored on the readable element includes any one or more of a manufacturer-specific authorization code, a cartridge batch identification code, and a usage history log for the cartridge.

17. A nebulizer as in claim 15, wherein the readable element storing the coded information comprises a barcode or punch code provided on an edge of the cartridge.

18. A nebulizer as in claim 15, wherein the readable element storing the coded information comprises a writable RFID tag.

19. A nebulizer as in claim 15, further comprising a control circuit adapted to disable operation, including of the drawing of liquid contents from the cartridge, whenever coded information read from the readable element indicates any one or more of an unauthorized cartridge, a refilled cartridge, any nonapproved contents in the cartridge, and an unauthorized user.

20. A nebulizer as in claim 19, wherein the control circuit is further adapted to record coded information including any one or more of a third-party establishment activation code for the nebulizer and a biometric user identifier.

21. A nebulizer comprising:
a nebulization chamber;
a liquid reservoir connected via a fluid flow path with a check valve to the nebulization chamber;
multiple discrete heating elements around the fluid flow path, wherein fluid from the liquid reservoir is heated in the fluid flow path to vaporization;
an inlet port coupled to an external air supply and leading through a Venturi nozzle into the nebulization chamber arranged to direct accelerated air across an opening of the fluid flow path in the nebulization chamber;
a discharge port leading from the nebulization chamber through an air pathway to a user mask; and
a filtered outlet port from the user mask.

22. A nebulizer as claim 21, wherein thermal insulation is provided between the discrete heating elements parallel to line of flow in the fluid flow path.

23. A nebulizer as in claim 21, wherein thermal insulation is provided radially outward around the heating elements to minimize heating of the liquid reservoir.

24. A nebulizer as in claim 21, wherein the fluid flow path has thermally conductive mesh therein at least at locations inwardly adjacent to the discrete heating elements.

25. A nebulizer as in claim 24, wherein wicking material is packed between the thermally conductive mesh.

26. A nebulizer as in claim 21, wherein the liquid reservoir has an air intake with a one-way valve to admit air into the reservoir while preventing leakage of fluid from the reservoir.

27. A nebulizer as in claim 21, wherein the user mask comprises a mouthpiece or a nasal canula that does not cover the mouth.

* * * * *